United States Patent
Jacobs et al.

(10) Patent No.: US 12,193,973 B2
(45) Date of Patent: Jan. 14, 2025

(54) DELIVERY DEVICE FOR ADMINISTERING FLUID TO AN EYE

(71) Applicant: SureDrops, LLC, Greenwood Village, CO (US)

(72) Inventors: Alan Jeffrey Jacobs, Greenwood Village, CO (US); Ian Daniel Jacobs, Greenwood Village, CO (US); Jennifer Adams Lello Jacobs, Greenwood Village, CO (US)

(73) Assignee: SureDrops, LLC, Greenwood Village, CO (US)

( * ) Notice: Subject to any disclaimer, the term of this patent is extended or adjusted under 35 U.S.C. 154(b) by 406 days.

(21) Appl. No.: 17/215,326

(22) Filed: Mar. 29, 2021

(65) Prior Publication Data

US 2022/0304855 A1 Sep. 29, 2022

(51) Int. Cl.
*A61F 9/00* (2006.01)
*A61B 3/14* (2006.01)
(Continued)

(52) U.S. Cl.
CPC .......... *A61F 9/0026* (2013.01); *G06T 7/0012* (2013.01); *G06T 7/70* (2017.01); *G06V 40/19* (2022.01); *G06V 40/193* (2022.01); *G08B 5/36* (2013.01); *A61B 3/14* (2013.01); *G06T 2207/30041* (2013.01)

(58) Field of Classification Search
CPC ....... A61F 9/0026; A61B 3/14; G06T 7/0012; G06T 7/70; G06T 2207/30041; G08B 5/36
See application file for complete search history.

(56) References Cited

U.S. PATENT DOCUMENTS 7,201,732 B2  4/2007  Anderson et al.
8,128,606 B2  3/2012  Anderson et al.
(Continued)

FOREIGN PATENT DOCUMENTS

EP            2490585 B1    5/2020
WO    WO 2020/214135 A1   10/2020

OTHER PUBLICATIONS

PCT International Search Report and Written Opinion, PCT Application No. PCT/US2022/021991, Jul. 26, 2022, 17 pages.
(Continued)

*Primary Examiner* — Leslie A Lopez
*Assistant Examiner* — Timothy L Flynn
(74) *Attorney, Agent, or Firm* — FENWICK & WEST LLP (57) ABSTRACT

A device includes an image capture device directed towards a user's eye and a dispensing mechanism configured to receive an apparatus containing fluid. The image capture device is coupled to a controller that processes images of the user's eye captured by the image capture device to determine when the user's eye has been open for at least a threshold amount of time. An orientation sensor included in the device determines an orientation relative to vertical of the device. When the controller determines that the user's eye has been open for at least a threshold amount of time and that the device has an orientation within a specific range, the dispensing mechanism applies force to the apparatus storing fluid to dispense fluid. One or more sensors in the device detect when fluid has been dispensed.

17 Claims, 7 Drawing Sheets

(51) Int. Cl.
*G06T 7/00* (2017.01)
*G06T 7/70* (2017.01)
*G06V 40/18* (2022.01)
*G06V 40/19* (2022.01)
*G08B 5/36* (2006.01)

(56) References Cited

U.S. PATENT DOCUMENTS

| | | |
|---|---|---|
| 9,610,192 B2 | 4/2017 | Marx |
| 2013/0006202 A1* | 1/2013 | Marx ................ A61F 9/0026 604/300 |
| 2014/0228783 A1 | 8/2014 | Kraft |
| 2016/0354240 A1 | 12/2016 | Chauhan et al. |
| 2018/0085251 A1* | 3/2018 | Hunter ............ B05B 17/0661 |
| 2018/0092772 A1* | 4/2018 | Mosalam ............ A61F 9/0008 |
| 2018/0193190 A1* | 7/2018 | Ajaelo .............. G16H 20/13 |
| 2019/0167096 A1 | 6/2019 | Voss et al. |
| 2022/0280338 A1* | 9/2022 | Böhme ............. A61F 9/008 |

OTHER PUBLICATIONS

European Patent Office, Extended European Search Report and Opinion, EP Patent Application No. 22781933.1, Nov. 22, 2024, ten pages.

* cited by examiner

DELIVERY DEVICE FOR ADMINISTERING FLUID TO AN EYE

BACKGROUND

This invention relates generally to dispensing fluid to a user's eye, and more specifically to a device for dispensing fluid into a user's eye based on a determination of whether the user's eye is open.

Various fluid dispensing apparatuses allow a user to dispense fluid to contact the user's eye, allowing users to apply fluid to the user's eye to treat medical conditions to aid in hydrating the user's eye. However, use of fluid dispensing apparatuses by users may have limited effectiveness, as users may have difficulty in positioning a fluid dispensing apparatus so fluid is dispensed into the user's eye. Further, users may have difficulty in dispensing fluid from a fluid dispensing apparatus before the user's eye blinks or otherwise closes, which prevents the dispensed fluid from contacting the surface of the user's eye.

SUMMARY

A device includes an image capture device directed towards a user's eye and includes a dispensing mechanism, which is configured to receive a bottle or other apparatus storing fluid to be administered to the user's eye. The image capture device captures images of the user's eye and is coupled to an image analysis module. From the captured images of the user's eye, the image analysis module determines when the user's eye has been open for at least a threshold amount of time. In various embodiments, the image analysis module identifies the pupil of the user's eye in the captured images and determines a duration that the pupil is visible in the captured images. The image analysis module determines that the user's eye has been open for at least the threshold amount of time when the image analysis module determines that duration that the pupil of the user's eye has been visible in captured images for at least the threshold amount of time.

Additionally, the device includes an orientation sensor configured to determine an orientation of the device relative to vertical. In some embodiments, the orientation sensor also determines whether the device is positioned over a user's right eye or over a user's left eye. The orientation sensor is also coupled to the controller. The orientation sensor and the image analysis module are coupled to a controller, which receives data from the orientation sensor and from the image analysis module. In response to determining the user's eye has been open for at least the threshold amount of time and that the orientation of the device relative to vertical is in a specific range, the controller transmits a control signal to the dispensing mechanism. In response to receiving the control signal, the dispensing mechanism applies force to the apparatus storing fluid to dispense fluid. In various embodiments, the apparatus storing fluid is inserted into a cartridge, with the cartridge including the apparatus storing fluid inserted into the dispensing mechanism. Inserting the apparatus dispensing fluid into the cartridge to standardize a distance between the apparatus storing fluid and the user's eye and to allow more uniform application of pressure to the apparatus storing fluid by the dispersing mechanism.

In various embodiments, a notification system is coupled to the controller. The notification system is configured to provide instructions to a user for positioning the eye cup. For example, the instructions describe movement of the eye cup so the orientation of the eye cup relative to vertical is within the range of orientations. In another embodiment, the instructions describe movement of the eye cup relative to the user's eye. The notification system may include a plurality of light sources each in different positions within the interior of the eye cup and illuminates a light source corresponding to a direction to move the eye cup relative to the user's eye, providing a visual instruction to the user of a direction in which to move the eye cup. In another embodiment, the notification system illuminates a light source corresponding to a direction to tilt the eye cup relative to vertical.

One or more sensors in the device (e.g., infrared sensors), detect when an amount of fluid has been dispensed from the apparatus storing fluid toward the user's eye. In some embodiments, the one or more sensors are coupled to the controller, which counts an amount of fluid (e.g., a number of drops) that has been dispensed. Data indicating an amount of fluid that have been dispensed, as well as images of the user's eye captured when fluid was dispensed, may be stored in association with an identifier of the user. For example, the device is coupled to a client device or other storage device that receives information from the controller including images of the user's eye and information about the amount of fluid dispensed towards the user's eye.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Device Architecture

Figure 1:
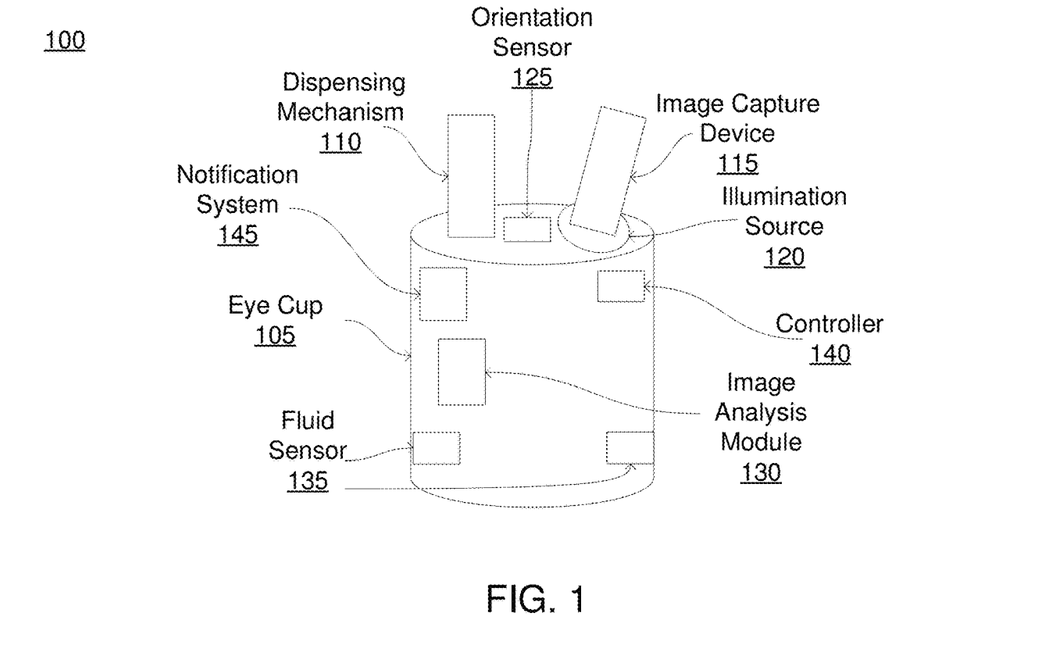
FIG. 1 is a block diagram of a delivery device for dispensing fluid to an eye of a user, in accordance with an embodiment.

FIG. 1 is a block diagram of a delivery device 100 for dispensing fluid to an eye of a user. In the embodiment shown by FIG. 1, the delivery device 100 comprises an eye cup 105, and a dispensing mechanism 110, an image capture device 115, an illumination source 120, an orientation sensor 125, an image analysis module 130, a fluid sensor 135, a controller 140, and a notification system 145 coupled to the eye cup 105. However, in other embodiments, the delivery device 100 includes different or additional components than those described in conjunction with FIG. 1. In some embodiments, modules or components described in conjunction with FIG. 1 are combined so a single component provides functionality of multiple components described in conjunction with FIG. 1.

The eye cup 105 is cylindrical in various embodiments with an opening at a first end of the eye cup and the dispensing mechanism 110 and the image capture device 115 coupled to a second end that is parallel or at an angle to the opening and separated from the opening by a distance. The eye cup 105 is configured so the opening encloses a user's eye, provides for positioning of the eye cup 105 relative to the user's eye, and provides a seal around a perimeter of the user's eye to reduce ambient light from a surrounding environment entering the interior of the eye cup 105. In various embodiments, the eye cup 105 is plastic; however, the eye cup 105 may be made from any suitable material in different embodiments. Further, the eye cup 105 is opaque to reduce light from the environment surrounding the eye cup 105 from entering the interior of the eye cup 105.

The dispensing mechanism 110 is coupled to the eye cup 105 on a surface of the eye cup 105 that is parallel or at an angle to an opening configured to enclose a user's eye. Additionally, the dispensing mechanism 110 is configured so an apparatus, such as a bottle, including fluid may be inserted into the dispensing mechanism 110. When the apparatus including fluid is inserted into the dispensing mechanism 110, an opening of the apparatus including fluid protrudes into the interior of the eye cup 105, allowing fluid from the apparatus to be dispensed into the interior of the eye cup 105. In another embodiment, there is an opening in the eyecup for passage of fluid from the apparatus to be dispensed into the interior of the eye cup 105. The dispensing mechanism 110 is configured to symmetrically apply force to a plurality of sides of the apparatus including fluid in response to receiving a control signal from the controller 140. For example, the dispensing mechanism 110 applies force to a plurality of opposing sides of the apparatus including fluid in response to receiving the control signal from the controller 140. However, in other embodiments, the dispensing mechanism 110 symmetrically applies force to any number (e.g., 3, 4, 5, etc.) of sides of the apparatus including fluid. Application of force by the dispensing mechanism 110 causes the apparatus including fluid to dispense fluid, such as one or more drops of fluid, into the interior of the eye cup 105. In various embodiments, the dispensing mechanism is configured to apply symmetrical bilateral force to regions on opposing sides of the apparatus including fluid in response to receiving the control signal from the controller 140, while in other embodiments the dispensing mechanism symmetrically applies force to regions on any number of different sides of the apparatus including fluid.

In some embodiments, the dispensing mechanism 110 is configured to receive a cartridge into which a fluid dispensing apparatus is inserted. This allows the dispensing mechanism 110 to more easily accommodate different shapes or sizes of fluid dispensing apparatuses, with the cartridge into which the fluid dispensing apparatus is inserted providing a standardized size to the dispensing mechanism 110 for applying force and maintaining a consistent distance between an opening of the fluid dispensing apparatus and the user's eye. Different cartridges may be configured to include different shapes or sizes of fluid dispensing apparatuses, with the different cartridges providing uniform dimensions for the dispensing mechanism 110 to apply force.

The image capture device 115 is configured to capture images of an interior of the eye cup 105 and is positioned so a portion of the user's eye is within a field of view of the image capture device 115 when an opening of the eye cup 105 is positioned over the user's eye 105. The image capture device 115 is coupled to the image analysis system 155 and transmits captured images to the image analysis system 155.

Figure 9:
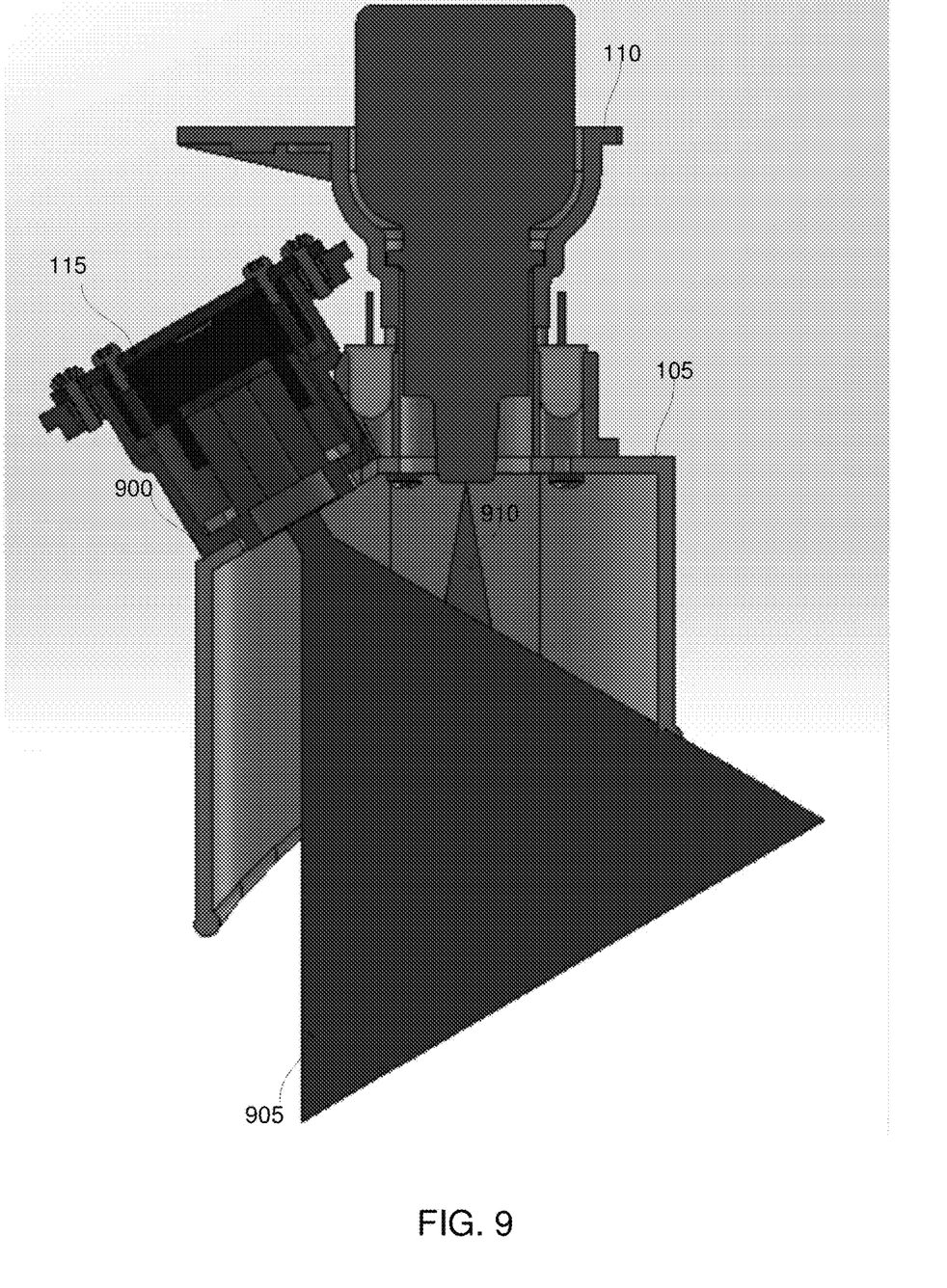
FIG. 9 is a cross-section of an eye cup to which an image capture device and a dispensing mechanism are coupled, in accordance with an embodiment.

FIG. 9 shows a cross-section of the delivery device 110 depicting an eye cup 105 to which the dispensing mechanism 110 and the image capture device 115 are coupled. As shown in FIG. 9, the image capture device 115 is coupled to a surface 900 of the eye cup 105 that has an angular orientation relative to a surface of the eye cup 105 to which the dispensing mechanism 110 is coupled. Positioning of the image capture device 115 on the surface 900 of the eye cup 105 is determined by one or more parameters of the image capture device 115, so the image capture device 115 is positioned so its field of view 905 includes the interior of the eye cup 105. This allows the field of view 905 of the image capture device 115 to include the interior of the eye cup 105 where the user's eye is positioned. In various embodiments, different image capture devices 115 having different fields of view 905 are positioned in different locations along the surface 900 so the field of view 905 of an image capture device 115 includes the interior of the eye cup 105. FIG. 9 also shows a drop range 910 identifying a range of locations within which a drop of fluid dispensed by a fluid containing apparatus included in the dispensing mechanism 110 is located at different locations within the eye cup 105.

Referring back to FIG. 1, an illumination source 120 is included in the interior of the eye cup 105 and is configured to illuminate the interior of the eye cup 105, including a user's eye when the user's eye is positioned in the opening of the eye cup 105. For example, the illumination source 120 comprises one or more light sources (e.g., light-emitting diodes (LEDs)) that emit light in the visible band (i.e., —380 nm to 750 nm), in the infrared (IR) band (i.e., —750 nm to 1 mm), in the ultraviolet band (i.e., 10 nm to 380 nm), in some other portion of the electromagnetic spectrum, or in some combination thereof. In some embodiments, different light sources included in the illumination source 120 have different characteristics. As an example, different light sources emit light having different wavelengths or different temporal coherences describing correlation between light waves at different points in time. Further, light emitted by different light sources may be modulated at different frequencies or amplitudes (i.e., varying intensity) or multiplexed in a time domain or in a frequency domain. In various embodiments the illumination source 120 comprises multiple light emitting diodes (LEDs), or other light sources, positioned at different locations relative to the image capture device 115. For example, the illumination source 120 is a ring of LEDs with the image capture device 115 at the center of the ring of LEDs. However, in other embodiments, the LEDs have any suitable positions within the interior of the eye cup 105.

The orientation sensor 125 is positioned on the eye cup 105 to have a known position relative to an orientation of the eye cup 105. In one embodiment the orientation sensor is an accelerometer that and generates a signal from accelerative force. As signal from the accelerometer 130 changes based on changes in orientation of the eye cup 105. The signal from the orientation sensor 125 and the known position of the orientation sensor 125 relative to the vertical orientation of the eye cup 105 allows determination of the orientation of the eye cup 105 relative to its vertical orientation. The orientation sensor 125 is coupled to the controller 140 so the signal generated by the orientation sensor 125 is received by the controller 140 for the controller 140 to determine the orientation of the eye cup 105 relative to its vertical orientation. Additionally, an additional signal from the orientation sensor 125 determines whether the eye cup 105 is positioned over a user's left eye or right eye in various embodiments. For example, positioning the eye cup 105 over a right eye of the user causes the orientation sensor 125 to have a first orientation relative to a reference plane, so the additional signal has a first value; when the eye cup 105 is repositioned and placed over a left eye of the user, the eye cup 105 has an opposite orientation relative to the reference plane, so the additional signal has a second value.

Images captured by the image capture device 115 are obtained by then image analysis module 130 that identifies whether the user's eye is open based on the characteristics recorded in the image. In various embodiments, the image analysis module 130 compares captured images of the user's eye to a collection of images of eyes (e.g., reference images) in a database. In one embodiment, the image analysis module 130 applies one or more trained models to the captured images to identify whether the user's eye is open. A model may be trained using images of eyes of one or more users that are each labeled with an indication of whether an eye in an image is opened or closed. Using any suitable training method or methods (e.g., supervised learning, semi-supervised learning, unsupervised learning) applied to the labeled images, one or more of the models are trained to identify whether an eye included in an image is open or closed based on characteristics of the eye included in the image. In other embodiments, the image analysis module 130 uses one or more characteristics recorded for the eye to identify whether the user's eye is open (e.g., via analysis of structural/physical properties, via use of an image of the user's eye, via use of images of other eyes, etc.). In addition, both comparison of captured images of the user's eye to a database and use of characteristics of the eye can be used to identify whether the user's eye is open in some embodiments In another embodiment, the image analysis system 130 identifies the position of the user's eye within the eye cup 105 from one or more characteristics recorded in the image (e.g., via analysis of structural/physical properties, via use of an image of the user's eye, via use of images of other eyes, etc.). In another embodiment, the image analysis module 130 identifies a position of a specific portion of the user's eye, such as the user's pupil, within eye cup 105. In another embodiment the image analysis module 130 identifies the location of the user's eyelids within the eye cup 105.

In some embodiments, the image analysis module 130 identifies characteristics of the user's eye, such as locations of points along the boundary of the user's eye, to determine whether images captured by the image capture device 115 include a user's right eye or a user's left eye. As an example, the image analysis module 130 identifies a caruncle of the user's eye included in captured images and determines whether the user's eye is the user's right eye or the user's left eye based on a location of the caruncle in the captured images. In some embodiments, the image analysis module 130 receives signals from the orientation sensor 125 and accounts for the signals from the orientation sensor 125 to determine whether the images include the user's left eye or right eye based on a signal received from the orientation sensor 125 based on an orientation of the eye cup 105 determined by the orientation sensor 125.

In various embodiments, the image analysis module 130 applies one or more trained models to the captured images to identify a pupil of the user's eye. For example, the image analysis module 130 identifies a region in the captured images having less than a threshold brightness and compares dimensions and shape of the identified region to one or more criteria to determine whether the identified region is the pupil of the user's eye. In various embodiments, the image analysis module 130 applies a machine learned model on previously captured images of users' eyes to features of the user's eye included in the captured images to identify the pupil of the user's eye. After identifying the pupil of the user's eye in captured images, the image analysis module 130 determines an amount of time that the pupil of the user's eye is visible in captured images.

In other embodiments, the image analysis module 130 uses any suitable processes to determines whether the user's eye is open from images captured by the image capture device 115. For example, the image analysis module 130 compares consecutive captured images of the user's eye and compares differences between the consecutive captured images to one or more thresholds to determine whether differences between the consecutive captured images indicate the user's eye has blinked. In other embodiments, the image analysis module 130 identifies any suitable features of the user's eye (e.g., an iris of the user's eye, the user's upper and lower eyelids) and determines whether the user's eye is open based on inclusion of different features in the captured images or positions of different features relative to each other in captured images. For example, the image analysis module 130 determines whether the user's eye is open if an iris of the user's eye is included in captured images for at least the threshold amount of time or if a distance between the upper and lower eyelids is at least a threshold distance for at least the threshold amount of time.

Additionally, from images obtained from the image capture device 115, the image analysis module 130 determines whether a portion of the user's eye is within a target area. For example, the image analysis module 130 determines whether a pupil of the user's eye is within the target area. The image analysis module 130 receives information describing the target area from the controller 140 in some embodiments but may receive information describing the target area from any suitable source in alternative embodiments. In various embodiments, the target area has a center point oriented to a center of the dispensing mechanism 110 and has a specified perimeter or a specified area. For example, the target area is a square or a rectangular region with a center point that is perpendicular to the center of the dispensing mechanism 110 and having a perimeter or an area specified by the controller 140. Alternatively, the target area is a circular or an elliptical region with a center point that is perpendicular to the center of the dispensing mechanism 110 and having an area or a circumference specified by the controller 140. In various embodiments, the image analysis module 130 or the controller 140 determines one or more dimensions of the target area based on a fluid containing apparatus inserted into the dispensing mechanism 110. This allows the controller 140 or the image analysis module to account for different types of fluid being dispensed by different fluid containing apparatuses and different dimensions of drops, or other amounts of fluid, dispensed by different fluid containing apparatuses. The controller 140 or the image analysis module 130 selects one or more dimensions for the target area stored in association with the received information identifying the fluid containing apparatus inserted into the dispensing mechanism 110.

The fluid sensor 135 is positioned between the opening of the eye cup 105 and the dispensing mechanism 110. In various embodiments, the fluid sensor 135 is a photoelectric sensor having a transmitter emitting light and a receiver configured to receive the emitted light. When the fluid sensor 135 comprises a photoelectric sensor, an amount of fluid, such as a drop, is detected when the fluid blocks light from the transmitter from reaching the receiver. In another embodiment, fluid is detected when the fluid reflects or refracts light from the transmitter. The fluid sensor 135 transmits an indication to the controller 140 when the fluid sensor 135 detected the presence of a fluid. In various embodiments, the fluid sensor 135 includes multiple photoelectric sensors with different orientations relative to each other, allowing the fluid sensor 135 to identify amounts of fluid traveling from the dispensing mechanism 110 to the user's eye at various locations within the interior of the eye cup 105.

The controller 140 receives data from the image analysis module 130 and from the orientation sensor 125. From the data from the image analysis module 130, the controller 140 determines whether the user's eye has been open for at least a threshold amount of time. From the data received from the image analysis module 130, the controller 140 receives an indication whether a portion of the user's eye is within a target location within the eye cup 105 and whether the user's eye is open. Additionally, from the data from the orientation sensor 130, the controller 140 determines whether the orientation of the eye cup 105 relative to vertical is such that an amount of fluid from the dispensing mechanism will reach a target location within the eye cup 105 at the user's eye. Based on the data from the image analysis system 155 and the orientation sensor 125, the controller 140 transmits a control signal to the dispensing mechanism 110 causing the dispensing mechanism 110 to apply force to an apparatus including fluid so fluid is dispensed from the apparatus to the user's eye through the interior of the eye cup 105.

From information received from the orientation sensor 130, the controller 140 determines an orientation of the eye cup 105 relative to vertical. The controller 140 maintains a range of orientations relative to vertical in which the dispensing mechanism 110 is capable of being activated. This range of orientations limits activation of the dispensing mechanism 110 to orientations of the eye cup 105 relative to vertical where a fluid, such as a drop of fluid, from the dispensing mechanism 110 has at least a threshold likelihood of contacting an eye of the user at the opening of the eye cup 105 in the target area, preventing the dispensing mechanism 110 from being activated and dispensing fluid when the eye cup 105 has an orientation where the fluid has less than the threshold likelihood of reaching the user's eye at the opening of the eye cup 105. As further described below in conjunction with FIG. 8, the controller 140 transmits a control signal to the dispensing mechanism 110 to apply force to a fluid containing apparatus included in the dispensing mechanism 110 in response to determining: (1) the user's eye at the opening of the eye cup 105 is open, (2) a portion of the user's eye is within a target area relative to the dispensing mechanism 110, and (3) an orientation of the eye cup 105 relative to vertical is within a range of orientations. This increases a likelihood of fluid dispensed from a fluid containing apparatus by the dispensing mechanism 110 contacting the user's eye.

In various embodiments, a notification system 145 is coupled to the controller 140. The notification system 145 is configured to provide instructions to a user for positioning the eye cup 105. For example, the instructions describe movement of the eye cup 105 so the orientation of the eye cup 105 relative to vertical is within the range of orientations. In another embodiment, the instructions describe movement of the eye cup 105 relative to the user's eye. Alternatively, the instructions describe movement of the user's head, such as instructions for a direction for the user to tilt the user's head. In some embodiments, the notification system 145 includes one or more speakers configured to present audible instructions to a user describing one or more directions in which to move the eye cup 105. Alternatively or additionally, the notification system 145 includes one or more light sources included in the interior of the eye cup 105, the notification system 145 illuminates a light source corresponding to a direction to move the eye cup 105 relative to the user's eye, providing a visual instruction to the user of a direction in which to move the eye cup 105. In another embodiment, the notification system 145 illuminates a light source corresponding to a direction to tilt the eye cup 105 relative to vertical. However, in other embodiments, the notification system 145 may provide instructions to the user for repositioning the eye cup 105 using any suitable format or combination of formats.

The notification system 145 also receives data from the orientation sensor 125 indicating whether the eye cup 105 is positioned over a user's left eye or right eye in various embodiments. For example, positioning the eye cup 105 over a right eye of the user causes the orientation sensor 125 to have a first orientation relative to a reference plane, so the additional signal has a first value; when the eye cup 105 is repositioned and placed over a left eye of the user, the eye cup 105 has an opposite orientation relative to the reference plane, so the additional signal has a second value. The notification system 145 uses the value of the additional signal to determine which lights to illuminate to direct user movement or which audio directions to provide to the user to move the eye cup 105. Hence, the value of the additional signal allows the notification system 145 to calibrate its instructions for movement based on which eye of the user over which the eye cup 105 is positioned.

In some embodiments, the notification system 145 provides notification to the user in response to other events. For example, the notification system 145 provides a notification in response to a signal from the controller 140 that the controller 140 received an indication from the fluid sensor 135 that fluid was detected. As an example, the notification system 145 illuminates a light having a specific color in response to the signal from the controller 140 that the fluid sensor 135 detected fluid. In another embodiment, the notification system 145 provides a notification to the user in response to receiving a signal from the image analysis module 130 that the portion of the user's eye is not within the target area. For example, the notification system 145 displays a specific color light or emits a specific audio signal in response to receiving the signal from the image analysis module 130 that the portion of the user's eye is not within the target area. Alternatively or additionally, the notification system 145 provides a notification to the user in response to receiving a signal from the image analysis module 130 that the portion of the user's eye is within the target area; the notification system 145 may present differing notifications to the user in response to the signal from the image analysis module 130 indicating that the portion of the user eye is within or is not within the target area.

Figure 2:
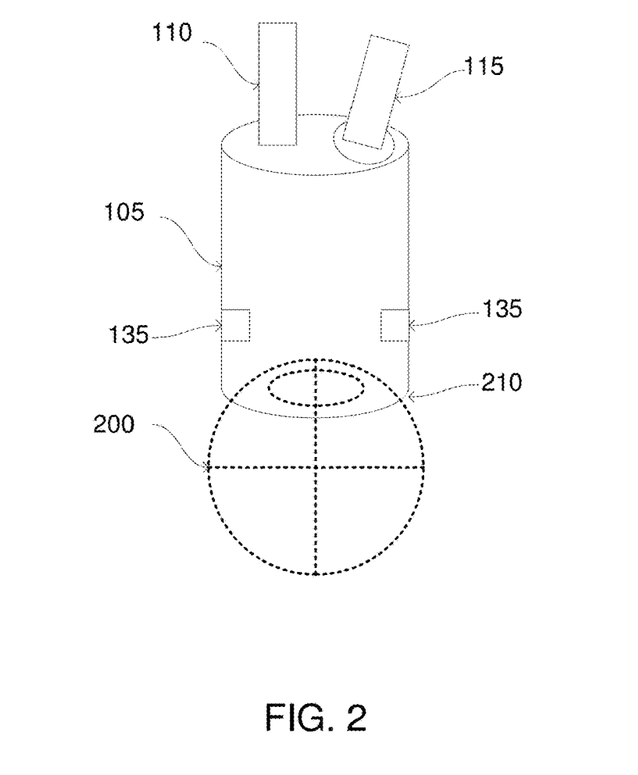
FIG. 2 is a cross section of a delivery device for dispending fluid to an eye of a user, in accordance with an embodiment.

FIG. 2 is a cross section of a delivery device for dispending fluid to an eye of a user. In the example of FIG. 2, the user's eye 200 is positioned at an opening 210 of the eye cup 105. When the user's eye 200 is included in the opening 210, the user's eye 200 is enclosed by the eye cup 105 so the user's eye 200 is in the interior of the eye cup 105, or at the opening 210 of the eye cup 105. As shown in FIG. 2, the user's eye 200 is in a plane that is parallel to a surface of the eye cup 105 onto which the dispensing mechanism 110 is coupled. Alternatively, the user's eye 200 is in a plane that is angled to a surface of the eye cup 105 onto which the dispensing mechanism 110 is coupled. Additionally, the image capture device 115 captures images of the user's eye 200 at the opening 210 of the eye cup 105. As further described above in conjunction with FIG. 1 and below in conjunction with FIG. 8, the image analysis module 130 receives the images of the user's eye 200 captured by the image capture device 115 and determines when the user's eye 200 is open and when a portion of the user's eye 200 is within a target area. The image analysis module 140 transmits data from the determinations to the controller 140, and in response to determining the user's eye 200 is open and the portion of the user's eye 200 is within the target area, as well as determining the eye cup 105 has an orientation relative to vertical that is within a range of orientations based on data from the orientation sensor 125, the controller 140 transmits a control signal to the dispensing mechanism 110. When the dispensing mechanism 110 receives the control signal, the dispensing mechanism 110 applies force to a fluid containing apparatus so fluid, such as a drop of fluid, is dispensed from the fluid containing apparatus. The fluid travels within the interior of the eye cup 105 to contact the user's eye 200. When travelling within the interior of the eye cup 105, the fluid is detected by a fluid sensor 135 that transmits a signal to the controller 140 indicating fluid was detected. This allows the controller 140 to store data indicating that the fluid was successfully dispensed and travelled through the interior of the eye cup 105. Hence, the controller 140 regulates when the dispensing mechanism 110 is activated to control when fluid is dispensed, increasing a likelihood of the fluid contacting the user's eye 200 while the user's eye 200 is open.

Eye Cup Configuration

Figure 3:
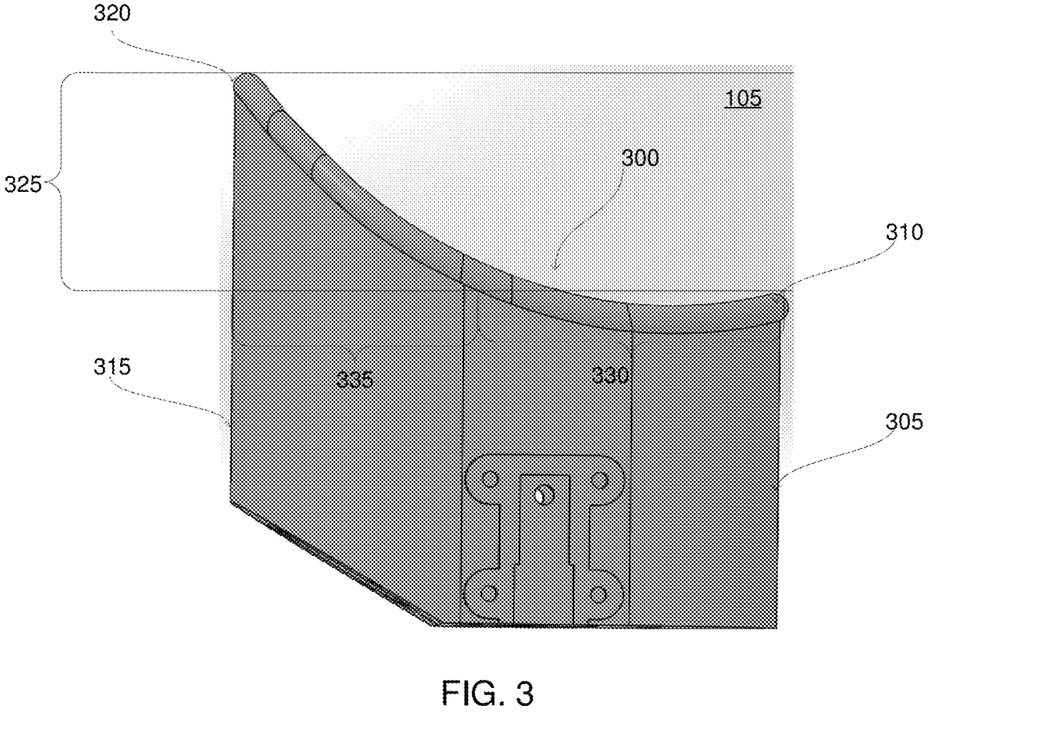
FIG. 3 is a side view an eye cup of a delivery device for dispensing fluid to a user's eye, in accordance with an embodiment.

FIG. 3 is a side view of one embodiment of the eye cup 105. In the embodiment shown by FIG. 3, the opening 300 of the eye cup 105 is oval, while in other embodiments the opening 300 of the eye cup 105 is circular or elliptical or any other suitable shape. The eye cup 105 has a first vertical side 305 contacting a first end 310 of the opening 300 and a second vertical side 315 contacting a second end 320 of the opening 300. The first vertical side 305 is parallel to the second vertical side 315 in various embodiments. The second end 320 of the opening 300 is in a plane having a specified distance 325 from the plane including the first end 310 of the opening 300, so the first end 310 and the second end 320 of the opening 300 are in different planes that are parallel to each other. The first end 310 of the eye cup 105 is configured such that it is positioned adjacent to the medial canthus of the user's eye. The second end 320 of the eye cup 105 is configured such that it is positioned adjacent to the lateral canthus of the user's eye. With an asymmetrical configuration of the eye cup 105, the orientation of the eye cup 105 is different when fitted to the user's left eye and right eye. In some embodiments, the controller 140 determines whether the user has placed the eye cup over the user's left eye or right eye based on the value of a signal from the orientation sensor 125 or based on analysis by the image analysis module 130 of images captured by the image capture device 115, as further described above in conjunction with FIG. 1. Additionally, the opening 300 curves so a portion 330 of the opening 300 is displaced away from the plane including the first end 310 of the opening 300 in an opposite direction than the second end 320 of the opening 300, then the opening 300 curves from the end of the portion 330 towards the plane including the first end 310 of the opening 300 then passes through the plane including the first end of the opening 310 until reaching the plane including the second end 320 of the opening 300. In various embodiments, such as the one shown in FIG. 3, the opening 300 has a second portion 335 adjacent to the portion 300, where the second portion 335 curves from the plane including the first end 310 of the opening 300 to the plane including the second end 320 with a curvature differing from a curvature of the portion 300. For example, the curvature of the second portion 335 is greater than the curvature of the portion 330. This allows the opening 300 of the eye cup 105 to snugly fit around a user's eye, so the user's eye is in the interior of the eye cup 105, allowing the eye cup 105 to minimize an amount of light from an environment surrounding the eye cup 105 that the eye cup 105 blocks from reaching the user's eye. The differing curvatures of the portion 300 and the second portion 330 result in an asymmetrical shape for the eye cup 105, causing an orientation of the eye cup 105, and of the orientation sensor 125 and the image capture device 115, when the eye cup 105 is positioned over a right eye of the user to differ from an orientation of the eye cup 105, and of the orientation sensor 125 and the image capture device 115, when the eye cup is positioned over a left eye of the user.

Figure 4:
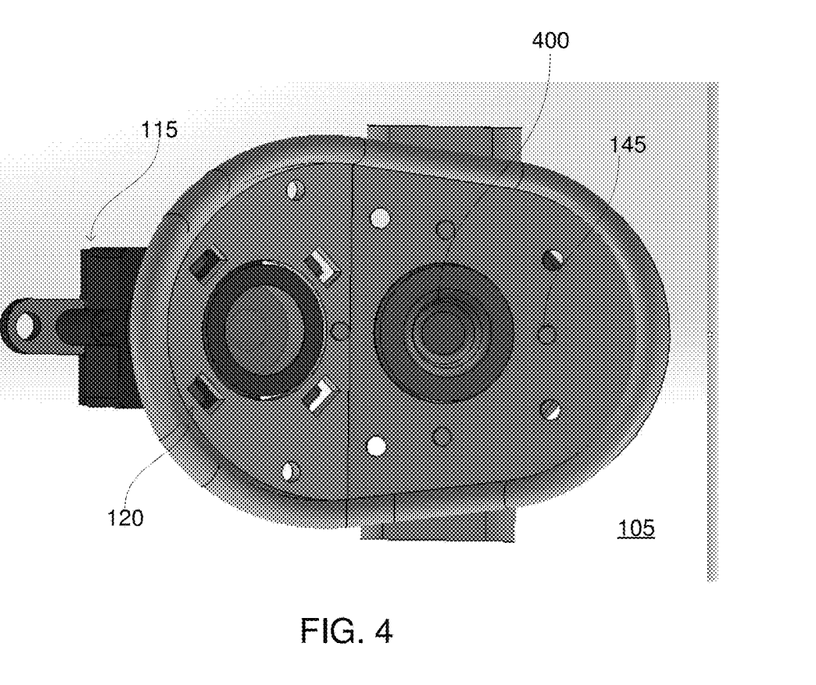
FIG. 4 is a view from an opening of an eye cup towards a surface of the eye cup onto which a dispensing mechanism is coupled, in accordance with an embodiment.

FIG. 4 is a view from an opening of the eye cup 105 towards a surface of the eye cup 105 onto which the dispensing mechanism 110 is coupled. As shown in FIG. 4, the image capture device 115 is positioned so the opening of the eye cup 105 is within a field of view of the image capture device 115, allowing capture of images of a user's eye when positioned at the opening of the eye cup 105. Additionally, FIG. 4 shows an embodiment of the illumination source 120 comprising multiple light sources, such as light emitting diodes (LEDs) positioned around a perimeter of the image capture device 115. In various embodiments, the illumination sourced 120 emits light having any suitable wavelength, such as infrared wavelengths, into the interior of the eye cup 105. This allows the illumination source 120 to illuminate the user's eye when positioned at the opening of the eye cup 105, improving the quality of images captured by the image capture device 115. In various embodiments, the illumination source 120 emits light in a band of wavelengths, such as light in infrared wavelengths, to allow a portion of the user's eye, such as a pupil of the user's eye, to be more easily identified within images captured by the image capture device.

FIG. 4 also shows a fluid containing apparatus 400 inserted into the dispensing mechanism 110. When inserted into the dispensing mechanism 110, an opening of the fluid containing apparatus 400 is included in the interior of the eye cup 105. This allows fluid dispensed from the fluid containing apparatus 400 by activation of the dispensing mechanism 110 to enter the interior of the eye cup 105 and travel towards the user's eye when the user's eye is positioned at the opening of the eyecup 105.

A notification system 145 shown in FIG. 4 comprises light sources having a plurality of positions in the eye cup 105. The light sources may emit light in one or more colors or using one or more patterns in various embodiments. For example, the notification system 145 shown in FIG. 4 includes four light sources positioned along a horizontal axis and a vertical axis each having an origin at the center of the fluid containing apparatus 400. As further described above in conjunction with FIG. 1, the notification system 145 receives control signals from the controller 140 and provides indications to a user for positioning the eye cup 105 so the orientation of the eye cup 105 relative to vertical is within the range of orientations relative to vertical 105. In various embodiments, the notification system 145 illuminates a light source to indicate a direction in which the user is to move the eye cup 105 and deactivates the illuminated light source in response to receiving a deactivation instruction from the controller 140 indicating the orientation of the eye cup 105 relative to vertical is within the range of orientations. The notification system 145 allows the controller 140 to guide a user to reposition the eye cup 105 to an orientation relative to vertical that is within the range of orientations in which the dispensing mechanism 110 is capable of being activated. In another embodiments, the notification system 145 illuminates a light source to indicate a direction in which the user is to move the eye cup 105 relative to the user's eye and deactivates the illuminated light source in response to receiving a deactivation instruction from the controller 140 indicating the position of the eye cup 105 relative to the user's eye is within a range of positions. The notification system 145 allows the controller 140 to guide a user to position the eye cup 105 to a position relative to the user's eye that is within the range of positions in which the dispensing mechanism 110 is capable of being activated. While FIG. 4 shows an example notification system 140 including four light sources positioned around the fluid dispensing apparatus 400, in other embodiments, the notification system 145 may include any suitable number of light sources that have any suitable orientation in the eye cup 105. Additionally, the notification system 145 may alternatively or additionally include one or more speakers that output audible instructions to the user describing directions for the user to position the eye cup 105 so an orientation of the eye cup 105 relative to vertical is within the range of orientations and a position of the eye cup 105 relative to the user's eye is within the range of positions.

Example Dispensing Mechanisms

Figure 5:
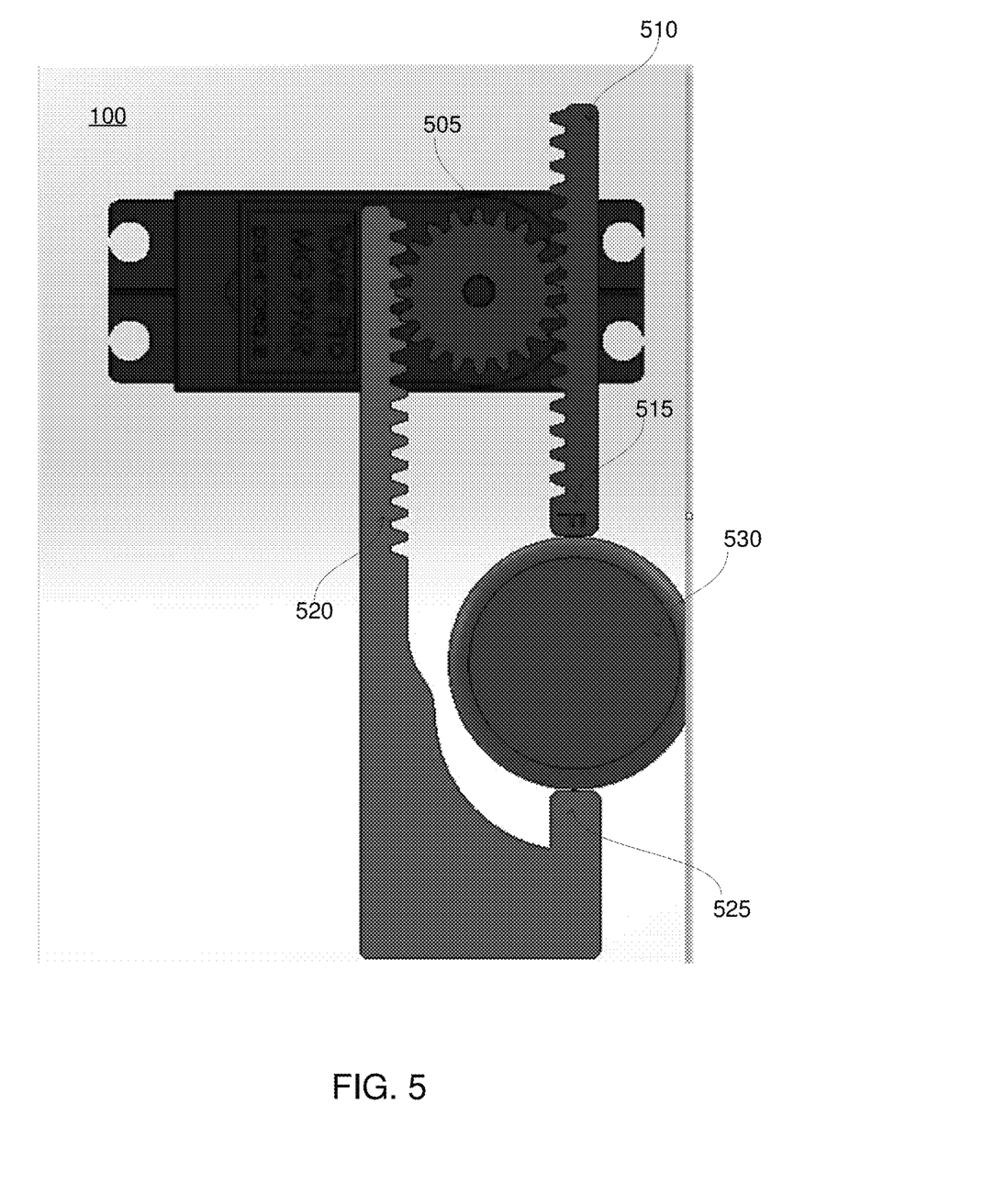
FIG. 5 is a dispensing mechanism including a rack and pinion configuration, in accordance with an embodiment.

FIG. 5 is an embodiment of a dispensing mechanism 110 including a rack and pinion configuration. In the embodiment shown by FIG. 5, a pinion 505 is engaged with a first rack 510 and a second rack 520. As the pinion 505 rotates in a direction, the first rack 510 moves in a first direction towards a fluid dispensing apparatus 530 so a contacting portion 515 of the first rack 510 moves towards a surface of the fluid dispensing apparatus 530 and contacts the surface of the fluid dispensing apparatus 530. Similarly, as the pinion 505 rotates in the direction, the second rack 520 moves in a second direction towards the fluid dispensing apparatus 530. The second direction in which the second rack 520 moves is opposite to the first direction in which the first rack 510 moves; hence, rotation of the pinion 505 moves an additional contacting portion 525 of the second rack 520 towards a second surface of the fluid dispensing apparatus 530 and contacts the second surface of the fluid dispensing apparatus 530. When the pinion 505 rotates in an opposite direction, the first rack 510 moves away from the fluid dispensing apparatus 530, while the second rack 520 similarly moves away from the fluid dispensing apparatus 530.

Figure 6:
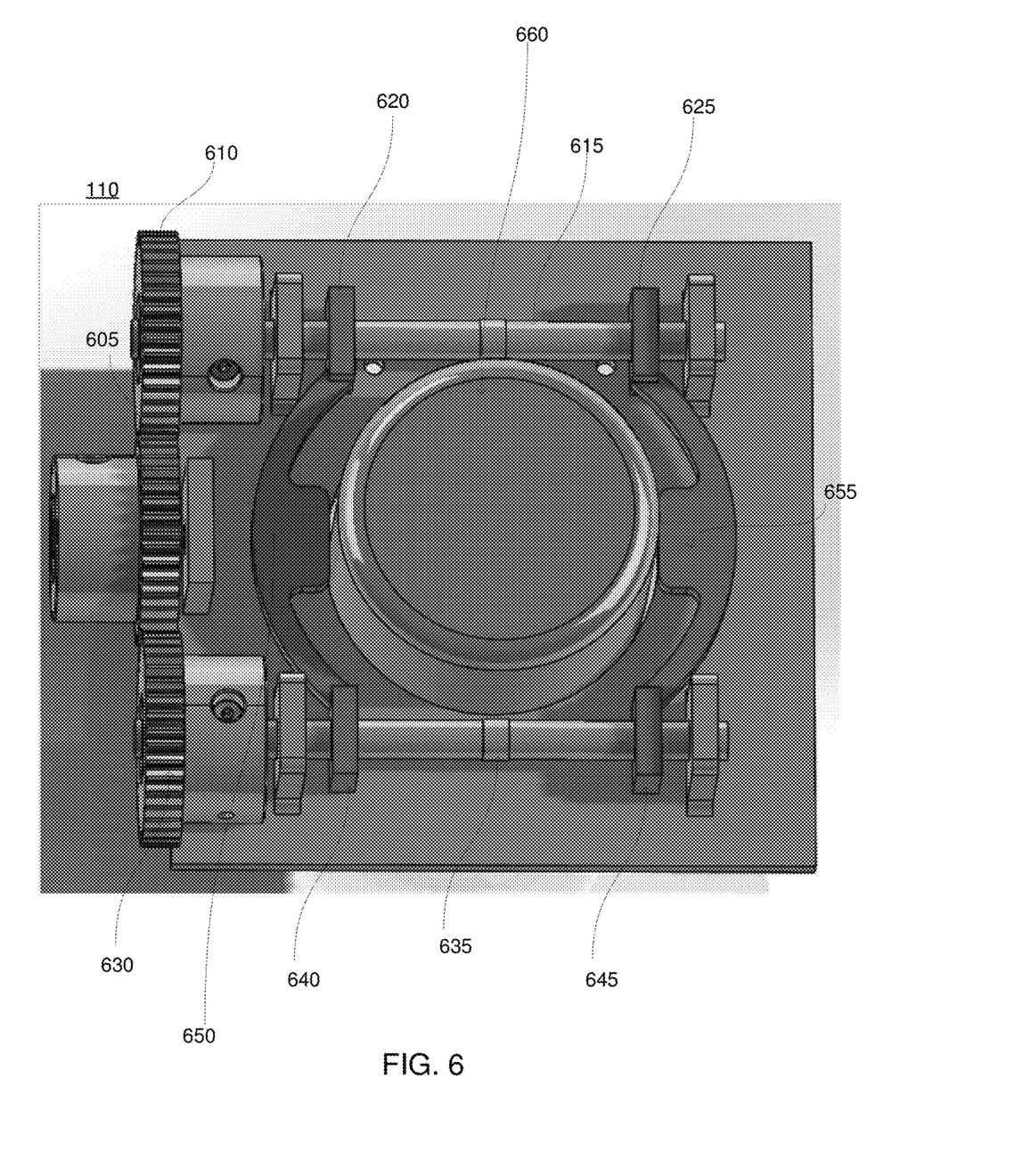
FIG. 6 is an alternative configuration of the dispensing mechanism, in accordance with an embodiment.

FIG. 6 is an alternative embodiment of the dispensing mechanism 110. In the embodiment shown by FIG. 6, the dispensing mechanism 110 comprises a primary gear 605 coupled to a secondary gear 610, with the primary gear 605 also coupled to an additional secondary gear 630. When the primary gear 605 rotates in a first direction (e.g., in response to a receiving a control signal from the controller 140), the secondary gear 610 rotates so an axle 615 coupled to the secondary gear 610 rotates. As the axle 615 rotates, a connector 620 moves along the axle 615 in a first direction, while an additional connector 625 moves along the axle in a second direction that is opposite the first direction. Hence, rotation of the axle 615 by the secondary gear 610 moves the connector 620 and the additional connector 625 towards each other. For example, the connector 620 is coupled to a portion of the axle 615 having right-handed threads, while the additional connector 625 is coupled to an alternative portion of the axle 615 having left-handed threads. As the connector 620 moves in the first direction, a contacting member 650 coupled to the connector 620 also moves in the first direction, while an additional contacting member 655 coupled to the additional connector 625 moves in the second direction. Thus, movement of the connector 620 and the additional connector 625 from rotation of the axle 615 causes the contacting member 650 and the additional contacting member 655 to move towards each other.

Similarly, rotation of the primary gear 605 in the first direction causes the additional secondary gear 630 to rotate so an additional axle 635 coupled to the additional secondary gear 630 rotates in an opposite direction of the secondary gear 610. As the additional axle 635 rotates, a connector 640 moves along the additional axle 635 in the first direction, while an additional connector 645 moves along the additional axle 635 in the second direction that is opposite the first direction. For example, the connector 640 is coupled to a portion of the additional axle 635 having left-handed threads, while the additional connector 645 is coupled to an alternative portion of the additional axle 635 having right-handed threads. Hence, rotation of the additional axle 635 by the additional secondary gear 630 moves the connector 620 and the additional connector 625 coupled to the additional axle 635 towards each other. As the connector 640 moves in the first direction, the contacting member 650, which is coupled to the connector 640 also moves in the first direction, while an additional contacting member 655 coupled to the additional connector 645 moves in the second direction. Thus, movement of the connector 640 and the additional connector 645 from rotation of the additional axle 635 causes the contacting member 650 and the additional contacting member 655 to move towards each other. A fluid containing apparatus 660 is positioned between the contacting member 650 and the additional contacting member 655 so movement of the contacting member 650 and the additional contacting member 655 towards each other causes the contacting member 650 and the additional contacting member 655 to contact and to apply pressure to opposing sides of the fluid containing apparatus 660.

When the primary gear 605 receives an alternative signal from the controller 140 and rotates in a second direction that is opposite the first direction, the secondary gear 610 and the additional secondary gear 630 rotate in opposite directions to those described above. This opposite rotation causes rotation of the axle 615 and of the additional axle 635 that moves the contacting member 650 and the additional contacting member 655 away from each other. When a fluid containing apparatus 660 is inserted between the contacting member 650 and the additional contacting member 655, movement of the contacting member 650 and the additional contacting member 655 away from each other stops application of pressure to the fluid containing apparatus 660 by the contacting member 650 and the additional contacting member 655.

Figure 7:
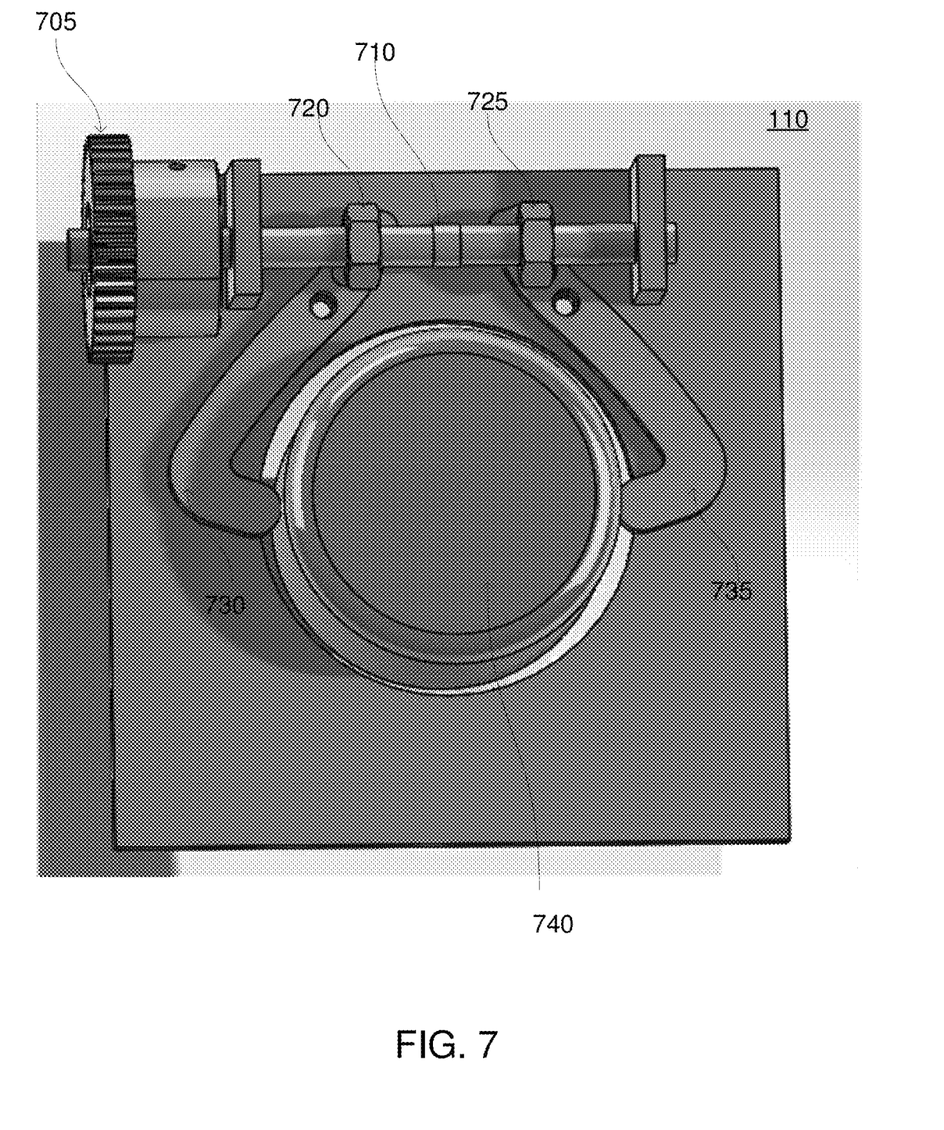
FIG. 7 is an additional configuration of the dispensing mechanism, in accordance with an embodiment.

FIG. 7 is an additional embodiment of a dispensing mechanism 110. In the embodiment shown by FIG. 7, the dispensing mechanism 110 comprises a gear 705 coupled to an axle 710. When the gear 705 rotates in a first direction (e.g., in response to a receiving a control signal from the controller 140), the gear 705 rotates, causing rotation of the axle 710 coupled to the gear 705 in the first direction. A connector 720 couples the axle 710 to a contacting member 720, while an additional connector 725 couples the axle to an additional contacting member 735. Rotation of the axle in the first direction causes the connector 720 and the additional connector 725 to move away from each other. In various embodiments, the connector 720 is coupled to a portion of the axle 710 having threads with a first direction, while the additional connector 720 is coupled to an alternative portion of the axle 710 having threads with a second direction that is opposite the first direction. For example, the connector 720 is coupled to a portion of the axle 710 having right-handed threads, while the additional connector 725 is coupled to an alternative portion of the axle 710 having left-handed threads. Movement of the connector 720 and the additional connector 725 away from each other along the axle causes an end of the contacting member 730 farthest from the connector 720 and an end of the additional contacting member 735 farthest from the additional connector 725 to move towards each other. When a fluid containing apparatus 740 is positioned between the contacting member 730 and the additional contacting member 735, movement of the end of the contacting member 730 farthest from the connector 720 and the end of the additional contacting member 735 farthest from the additional connector 725 toward each other causes the end of the contacting member 730 farthest from the connector 720 and the end of the additional contacting member 735 farthest from the additional connector 725 to contact opposing sides of the fluid containing apparatus 740, applying pressure to the fluid containing apparatus 740.

In response to an alternative signal from the controller 140, the gear 705 rotates in a second direction that is opposite the first direction, causing rotation of the axle 710 in the second direction. This causes the connector 720 and the additional connector 725 to move towards each other, moving causes an end of the contacting member 730 farthest from the connector 720 and an end of the additional contacting member 735 farthest from the additional connector 725 away from each other. When a fluid containing apparatus 740 is positioned between the contacting member 730 and the additional contacting member 735, movement of the end of the contacting member 730 farthest from the connector 720 and the end of the additional contacting member 735 farthest from the additional connector 725 toward each other away from each other causes s the end of the contacting member 730 farthest from the connector 720 and the end of the additional contacting member 735 farthest from the additional connector 725 to move away from the fluid containing apparatus 740, relieving pressure applied to the fluid containing apparatus 740

Dispensing Fluid to a User's Eye

Figure 8:
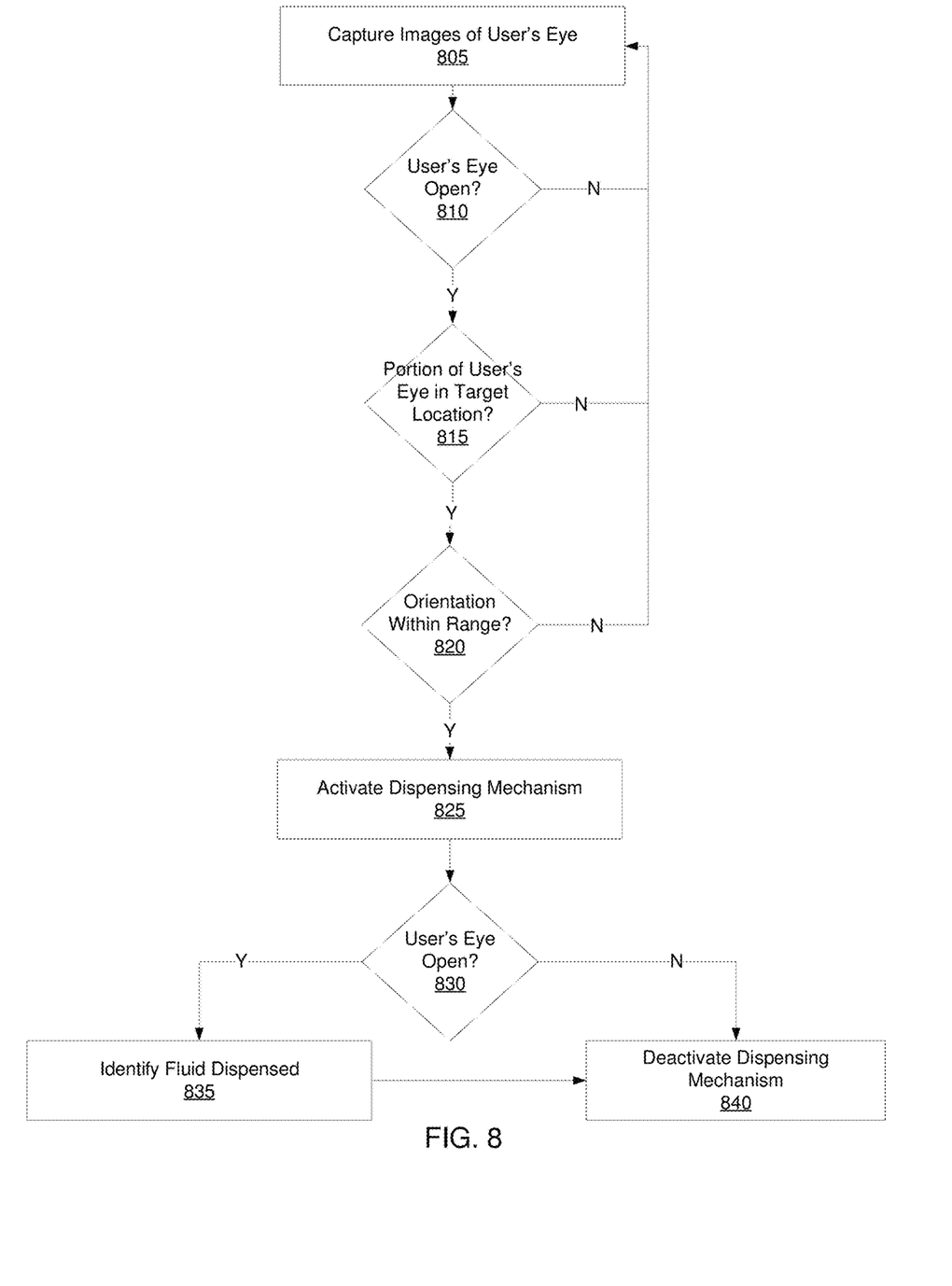
FIG. 8 is a flow chart of a method for dispensing fluid to an eye of a user, in accordance with an embodiment.

FIG. 8 is a flowchart of a method for dispensing fluid to a user's eye based on images of the user's eye and orientation of the eye cup 105. In various embodiments, the method includes different or additional steps than those described in conjunction with FIG. 8. Further, in some embodiments, the method performs the steps of the method in different orders than the order described in conjunction with FIG. 8.

When a user's eye is positioned at an opening of an eye cup 105, as further described above in conjunction with FIGS. 1-4, an image capture device 115 captures 805 images of the user's eye. The captured images are communicated to an image analysis module 130 coupled to the image capture device 115, and the image analysis module 130 determines 810 whether the user's eye is open. As further described above in conjunction with FIG. 1, the image analysis module 130 analyzes the captured images to identify one or more features of the user's eye and uses the identified features to determine whether the user's eye is open. The controller 140 receives data form the image analysis module 130 and compares an amount of time that the image analysis module 130 determines the user's eye is open to a threshold amount of time. In response to the amount of time that the user's eye is open being less than the threshold amount of time, the controller 140 determines 810 the user's eye is not open, so the image capture device 115 captures 805 additional images of the user's eye that are analyzed by the image analysis module 130. However, in response to the amount of time the user's eye is open equaling or exceeding the threshold amount of time, the controller 140 determines 810 the user's eye is open.

In response to determining 810 the user's eye is open, the controller 140 determines 815 whether a portion of the user's eye is in a target location while the user's eye is open. The target location has a center point perpendicular or at an angle to a center of a dispensing mechanism 110 included in the eye cup 105 and has a specified perimeter or a specified area. For example, the target location is a square region or a rectangular region with a center point that is perpendicular to the center of the dispensing mechanism 110 and having a perimeter or an area specified by the controller 140. Alternatively, the target location is a circular or an elliptical region with a center point that is perpendicular to the center of the dispensing mechanism 110 and having an area or a circumference specified by the controller 140. In various embodiments, the controller 140 determines one or more dimensions of the target area based on a fluid containing apparatus inserted into the dispensing mechanism 110 by retrieving stored dimensions of the target area stored in association with information identifying the fluid containing apparatus. This allows the controller 140 to account for different types of fluid being dispensed by different fluid containing apparatuses and different dimensions of drops or amounts of fluid dispensed by different fluid containing apparatuses.

In various embodiments, the controller 140 or the image analysis module 130 determines 815 whether an identified feature of the user's eye from captured images is within the target location. For example, the controller 140 determines 815 whether a pupil of the user's eye identified from the captured images is within the target location while the user's eye is open. As another example, the controller 140 determines 815 whether an iris of the user's eye identified from the captured images is within the target location while the user's eye is opened. The controller 140 compares a location of one or more features of the user's eye in the captured images to the target location determined by the controller 140 to determine 815 whether the one or more identified features of the user's eye are in the target location while the user's eye is open. In response to determining 815 a portion of the user's eye is not within the target location while the user's eye is open, additional images of the user's eye are captured 805 are processed by the controller 140 to determine 810 whether the user's eye is open and whether the portion of the user's eye is within the target location.

In response to determining 815 the portion of the user's eye is within the target location while the user's eye is open, the controller 140 determines 820 whether the eye cup 105 has an orientation relative to vertical that is within a range of orientations. From information received from the orientation sensor 125, the controller 140 determines an orientation of the eye cup 105 relative to vertical. The controller 140 maintains a range of orientations relative to vertical in which the dispensing mechanism 110 is capable of being activated. This range of orientations limits activation of the dispensing mechanism 110 to orientations of the eye cup 105 relative to vertical where fluid from the dispensing mechanism 110 has at least a threshold likelihood of contacting an eye of the user at the opening of the eye cup 105 in the target area, preventing the dispensing mechanism 110 from being activated and dispensing fluid when the eye cup 105 has an orientation where the fluid has less than the threshold likelihood of reaching the user's eye at the opening of the eye cup 105.

In some embodiments, if the controller 140 determines 820 the orientation of the eye cup 105 relative to vertical is not within the range of orientations, the controller 140 transmits instructions to the notification system 145. Based on the instructions, the notification system 145 provides instructions to the user to reposition the eye cup 105 to change the orientation of the eye cup 145 relative to vertical. For example, the notification system 145 includes one or more speakers configured to provide audible instructions to the user describing directions in which to move the eye cup 105 to change the orientation of the eye cup 105 relative to vertical. In another example, the notification system 145 includes one or more light sources in the interior of the eye cup 105, and the notification system 145 illuminates a light source corresponding to a direction in which the eye cup 105 is to be moved to change the orientation of the eye cup 105 relative to vertical. The notification system 145 may use a combination of the audible instructions and illumination of a light source in the interior of the eye cup 105 to provide instructions to the user for repositioning the eye cup 105 to a different orientation relative to vertical. Further, in other embodiments, the notification system 145 may use any suitable type, or combination of types, of feedback to provide instructions for repositioning the eye cup 105 to change its orientation relative to vertical. The image capture device 115 continues capturing 805 images of the user's eye when the controller 140 determines 820 the orientation of the eye cup 105 relative to vertical is not within the range of orientations, with the captured images analyzed to determine 810 whether the user's eye is open and to determine 815 whether a portion of the user's eye is within the target area, as further described above.

In response to determining 820 the orientation of the eye cup 105 is within the range of orientations relative to vertical, the controller 140 activates 825 a dispensing mechanism 110 coupled to a surface of the eye cup 105 parallel to the opening of the eye cup 105 where the user's eye is positioned, as further described above in conjunction with FIG. 1. To activate 825 the dispensing mechanism 110, the controller transmits a control signal to the dispensing mechanism 110, which applies pressure to a fluid containing apparatus included in the dispensing mechanism 110 in response to receiving the control signal. Examples of the dispensing mechanism 110 are further described above in conjunction with FIGS. 5-7. When the dispensing mechanism 110 applies force to the fluid containing apparatus, the force is symmetrically applied to multiple surfaces of the fluid containing apparatus. In various embodiments, the dispensing mechanism 110 bilaterally applies force to opposing surfaces of the fluid containing apparatus. The dispensing mechanism 110 may symmetrically apply force to opposing surfaces of the fluid containing apparatus in various embodiments. In various embodiments, the dispensing mechanism 110 is configured to apply force to relatively small areas on opposing surfaces of the fluid containing apparatus, with force applied to one surface of the fluid containing apparatus within a threshold amount of time of force being applied to the opposing surface of the fluid containing apparatus.

Application of force to the fluid containing apparatus by the dispensing mechanism 110 causes the fluid containing apparatus to dispense fluid into the interior of the eye cup. To account for an amount of time for the fluid to be dispensed from the fluid containing apparatus after force is applied and for the drop to travel through the interior of the eye cup 105 to the user's eye, the controller 140 determines 830 whether the user's eye remains open while the dispensing mechanism 110 is activated from images captured by the image capture device 115. The processes further described above are used by the controller 140 to determine 830 whether the user's eye remains open. If the controller 140 determines 830 the user's eye remains open while the dispensing mechanism 110 is activated 825, the dispensing mechanism 110 continues to apply pressure to the fluid containing apparatus.

In response to determining 830 that the user's eye is not open, or the orientation is not in range, or the portion of the user's eye is not within the target area when the dispensing mechanism 110 is activated, the controller 140 deactivates 840 the dispensing mechanism 110. For example, the controller 140 transmits an alternative control signal to the dispensing mechanism 110, which stops applying force to the fluid containing apparatus in response to receiving the alternative control signal. In some embodiments, the dispensing mechanism 110 pauses application of force to the fluid containing apparatus when receiving the alternative control signal, so the dispensing mechanism 110 subsequently resumes application of force from the position where the dispensing mechanism 110 paused; however, in other embodiments, the dispensing mechanism 110 resets to a starting position in response to receiving the alternative control signal. The controller 140 subsequently transmits an activation signal to the dispensing mechanism 110 after determining 805 that the user's eye is again open, determining 810 that the portion of the user's eye is within the target area, and determining 815 that the orientation of the eye cup 105 relative to vertical is within the range of orientations. By monitoring whether the user's eye remains open, the orientation is in range, and the portion of the user's eye is within the target area when the dispensing mechanism 110 is activated, the controller 140 prevents the fluid containing apparatus from dispensing fluid to the user's eye when the fluid would not reach the intended target area of the user's eye.

In another embodiment, the controller 140 determines whether the orientation of the eye cup 105 relative to vertical is within the range of orientations from information received from the orientation sensor 125 while the dispensing mechanism 110 is activated. By monitoring whether the orientation is within range when the dispensing mechanism 110 is activated, the controller 140 prevents the fluid containing apparatus from dispensing fluid to the user's eye while the orientation is not in the range or orientations. If the controller 140 determines the orientation is within the range of orientations while the dispensing mechanism 110 is activated 825, the dispensing mechanism 110 continues to apply pressure to the fluid containing apparatus. If the controller 140 determines the orientation is not in the range of orientations while the dispensing mechanism 110 is activated 825, the controller 140 deactivates the dispensing mechanism 110 via a deactivation signal transmitted to the dispensing mechanism 110. Subsequent to deactivation of the dispensing mechanism 110, images of the user's eye are captured 805 and analyzed, as further described above, to determine when the dispensing mechanism 110 is again activated. By monitoring whether the orientation remains in the range of orientations when the dispensing mechanism 110 is activated, the controller 140 prevents the fluid containing apparatus from dispensing fluid to the user's eye while the orientation is not in the range of orientations.

In another embodiment, the controller 140 determines whether the portion of the user's eye is within the target area while the dispensing mechanism 110 is activated. By monitoring whether the portion of the user's eye is within the target area when the dispensing mechanism 110 is activated, the controller 140 prevents the fluid containing apparatus from dispensing fluid to the user's eye when the portion of the user's eye is not within the target area. If the controller 140 determines the portion of the user's eye is not within the target area while the dispensing mechanism 110 is activated 825, the controller 140 deactivates the dispensing mechanism 110, while the dispensing mechanism 110 remains activated if the controller 140 determines the portion of the user's eye is within the target area while the dispensing mechanism is activated 825. Subsequent to deactivation of the dispensing mechanism 110, images of the user's eye are captured 805 and analyzed, as further described above, to determine when the dispensing mechanism 110 is again activated. By monitoring whether the portion of the user's eye is within the target area when the dispensing mechanism 110 is activated, the controller 140 prevents the fluid containing apparatus from dispensing fluid to the user's eye when the portion of the user's eye is not within the target area.

A fluid sensor 135 included in the interior of the eye cup 105 determines when an amount of fluid dispensed by the fluid containing apparatus in response to the force applied by the dispensing mechanism 110 travels past a specific location in the interior of the eye cup 105. For example, the fluid sensor 135 determines when an amount of fluid travels past the specific location in the interior of the eye cup 105. The fluid sensor 135 identifies 835 that the amount of fluid was dispensed from the fluid containing apparatus to the controller 140 in response to the fluid sensor 135 determining that the fluid has traveled past the specific location in the interior of the eye cup 105. In various embodiments, in response to the fluid sensor 135 identifying the fluid, the controller 140 transmits an alternative control signal to the dispensing mechanism 110 that deactivates the dispensing mechanism 110.

In some embodiments, the controller 140 stores a count of an amount of fluid, such as a number of drops, identified 835 by the fluid sensor 135 in association with an identifier of a user of the eye cup. The controller 140 may also store information identifying the fluid contained in the fluid containing apparatus in association with the amount of fluid identified 835 by the fluid sensor 135 and with the identifier of the user. Additionally, the controller 140 may store an image captured by the image capture device 115 corresponding to a time when the fluid sensor 135 identified 835 the fluid or corresponding to a specified amount of time after the time when the fluid sensor 135 identified 835 the fluid, in association with the identifier of the user, so an image of the fluid reaching the user's eye is stored in association with the identifier of the user. For example, the controller 140 receives a signal from the fluid sensor 135 when the fluid sensor 125 identifies 835 an amount of fluid and stores an image captured by the image capture device 115 at a time when the controller 140 receives the signal from the fluid sensor 125. The controller 140 may also store an indication of whether the stored image includes the user's right eye or the user's left eye, based on a determination from the orientation sensor 125 or the image analysis module 130, as further described above in conjunction with FIG. 1, allowing the controller 140 to identify which eye of the user received the dispensed fluid. Stored information describing fluid dispensed by the fluid containing apparatus by the dispensing mechanism 110 may be provided to one or more other users that the user of the eye cup 105 has authorized to access, such as a medical provider of the user of the eye cup 105.

Information stored by the controller 140 describing the amount of fluid identified 835 as dispensed, images of the eye captured 805 at times relative to the fluid sensor 135 detecting 835 fluid may be later accessed by a user or other users authorized by the user via the controller 140. Additionally, information describing identified amounts of fluid, as well as the fluid that was dispensed, may be communicated from the controller 140 to a client device, such as a computer or other device, via any suitable wired or wireless connection between the controller 140 and the client device. For example, the controller 140 transmits information identifying the fluid that was dispensed, an amount of the fluid identified 835 by the fluid sensor 135, and dates or times when the fluid was identified 835 to the client device. An application executing on the client device provides information about the drops identified 835 by the fluid sensor. For example, the application displays records identifying the fluid that was dispensed, an amount of the fluid that was dispensed, and a date or a time when the fluid was dispensed. The application may compare stored information describing recommended or prescribed dosages of the fluid that was dispensed and identify dates or times when the identified amount of fluid that was dispensed deviates from the recommended or prescribed dosages by at least a threshold amount. In some embodiments, the application transmits a message to the user or to another user (e.g., a medical provider of the user or other user that the user to whom the user has authorized access) in response to the identified amount of fluid that was dispensed deviates from the recommended or prescribed dosages by at least a threshold amount. A user authorized to access the information captured by the controller may also review stored data identifying the fluid that was dispensed, an amount of the fluid that was dispensed, and a date or a time when the fluid was dispensed to determine if the user has complied or satisfied dosage recommendations or requirements for dispensing the identified fluid.

Additional Configuration Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. An apparatus comprising:
    an eye cup having an opening configured to enclose an eye of a user, the eye cup having an asymmetrical shape so the eye cup has a different orientation when positioned over a right eye of the user than when positioned over a left eye of the user;
    a dispensing mechanism configured to receive an apparatus containing fluid and positioned so an opening of the apparatus containing fluid opens into an interior of the eye cup, the dispensing mechanism further configured to symmetrically apply force to a plurality of sides of the apparatus containing fluid when activated;
    an image capture device configured to capture images of the eye of the user;
    an orientation sensor configured to determine an orientation of the eye cup;
    an image analysis system coupled to the image capture device configured to:
        determine whether the eye of the user is open from images of the eye of the user captured by the image capture device; and
        determine whether a portion of the eye of the user is within a target area from images of the eye of the user captured by the image capture device;
    a controller coupled to the dispensing mechanism, to the image analysis system, and to the orientation sensor, the controller configured to:
        activate the dispensing mechanism in response to: (1) determining the eye of the user is open, (2) determining the portion of the eye of the user is within the target area, and (3) determining the orientation of the eye cup is within a specific range of orientations; and
        while the dispensing mechanism is activated, deactivate the dispensing mechanism in response to: (1) determining the eye of the user is not open, (2) determining the portion of the eye of the user is not within the target area, or (3) determining the orientation of the eye cup is not within a specific range of orientations.

2. The apparatus of claim 1, wherein the portion of the eye of the user is the pupil of the eye of the user.

3. The apparatus of claim 1, wherein the orientation sensor is further configured to determine whether the eye cup is positioned over the left eye or over the right eye of the user.

4. The apparatus of claim 1, wherein the image analysis system is configured to determine whether the eye of the user is the right eye of the user or the left eye of the user based on characteristics of the eye of the user in the captured images.

5. The apparatus of claim 1, further comprising:
    a fluid sensor positioned at a location between the dispensing mechanism and the opening of the eye cup, the fluid sensor configured to transmit an indication to the controller when the fluid sensor identifies fluid dispensed from the fluid containing apparatus.

6. The apparatus of claim 5, wherein the controller is further configured to:
    deactivate the dispensing mechanism in response to receiving the indication from the fluid sensor.

7. The apparatus of claim 5, wherein the controller is further configured to store one or more images captured by the image capture device when the controller receives the indication from the fluid sensor.

8. The apparatus of claim 1, further comprising:
    a notification system coupled to the controller, the notification system configured to provide instructions to the user.

9. The apparatus of claim 8, wherein the notification system is configured to provide instructions to the user in response to the controller determining the orientation of the eye cup is not within the specific range of orientations.

10. The apparatus of claim 8, wherein the notification system is configured to provide instructions to the user in response to determining the portion of the eye of the user is not within the target area.

11. The apparatus of claim 8, wherein the notification system is configured to provide notification to the user in response to the controller receiving an indication from a fluid sensor positioned at a location between the dispensing mechanism and the opening of the eye cup that the fluid sensor identified fluid from the fluid containing apparatus.

12. The apparatus of claim 8, wherein the notification system includes a plurality of light sources included in an interior of the eye cup, the notification system configured to illuminate a light source corresponding to a direction to move the eye cup.

13. The apparatus of claim 8, wherein the notification system includes a plurality of light sources included in an interior of the eye cup, the notification system configured to illuminate a light source corresponding to a direction for the user to tilt the head of the user.

14. The apparatus of claim 1, wherein the dispensing mechanism is configured to receive a cartridge into which the fluid containing apparatus is inserted, the cartridge configured to standardize a distance between the apparatus containing fluid and the eye of the user and to allow more uniform application of pressure to the apparatus containing fluid by the dispensing mechanism.

15. A method comprising:
  capturing images of an eye of a user included in an opening of an eye cup enclosing the eye of the user the eye cup having an asymmetrical shape so the eye cup has a different orientation when positioned over a right eye of the user than when positioned over a left eye of the user;
  determining whether the eye of the user is the right eye of the user or the left eye of the user;
  determining whether the eye of the user is open from the captured images;
  determining whether a portion of the eye of the user is within a target area from the captured images;
  determining whether an orientation of the eye cup received from an orientation sensor coupled to the eye cup is within a range of orientations;
  transmitting a control signal to activate a dispensing mechanism coupled to a surface of the eye cup opposite the opening enclosing the eye of the user in response to: (1) determining the eye of the user is open, (2) determining the portion of the eye of the user is within the target area, and (3) determining the orientation of the eye cup relative is within the range of orientations; and
  while the dispensing mechanism is activated, transmitting a control signal to deactivate the dispensing mechanism in response to: (1) determining the eye of the user is not open, (2) determining the portion of the eye of the user is not within the target area, or (3) determining the orientation of the eye cup is not within a specific range of orientations.

16. The method of claim 15, further comprising:
storing an indication that the fluid was dispensed in association with an identifier of the user, the indication including an image captured by an image capture device when the indication was received and whether the image captured by the image capture device when the indication was received includes the left eye or the right eye of the user.

17. The method of claim 15, further comprising:
receiving an indication fluid was dispensed from a fluid containing apparatus received by the dispensing mechanism in response to activation of the dispensing mechanism, wherein the indication is received from a fluid sensor monitoring an interior of the eye cup in response to the fluid sensor sensing fluid that has been dispensed from the fluid containing apparatus.

* * * * *